(12) United States Patent
Sugiyama et al.

(10) Patent No.: US 7,378,237 B2
(45) Date of Patent: May 27, 2008

(54) DEVELOPMENT OF METHOD FOR SCREENING PHYSIOLOGICALLY ACTIVE PYRROLE IMIDAZOLE DERIVATIVE

(75) Inventors: Hiroshi Sugiyama, Tokyo (JP); Isao Saito, Kyoto (JP); Hirokazu Iida, Tokyo (JP)

(73) Assignee: Japan Science & Technology Corporation, Saitama (JP)

( * ) Notice: Subject to any disclaimer, the term of this patent is extended or adjusted under 35 U.S.C. 154(b) by 458 days.

(21) Appl. No.: 10/285,030

(22) Filed: Nov. 1, 2002

(65) Prior Publication Data

US 2003/0099998 A1     May 29, 2003

Related U.S. Application Data

(62) Division of application No. 09/889,379, filed as application No. PCT/JP00/07992 on Nov. 13, 2000, now Pat. No. 6,974,668.

(30) Foreign Application Priority Data

Nov. 16, 1999   (JP)   ................... 11-326007

(51) Int. Cl.
*C12Q 1/68*   (2006.01)
*A61K 49/00*   (2006.01)
*A61K 31/70*   (2006.01)
*A61K 39/395*   (2006.01)

(52) U.S. Cl. .................. 435/6; 424/9.1; 424/174.1; 514/44

(58) Field of Classification Search .............. 435/6; 434/9.1, 174.1; 514/44
See application file for complete search history.

(56) References Cited

U.S. PATENT DOCUMENTS 5,273,991 A * 12/1993 Lee .............................. 514/397
6,713,633 B1 * 3/2004 Sugiyama et al. .......... 548/416

FOREIGN PATENT DOCUMENTS

WO   WO-00/58312   10/2000
WO   WO 00/58312 A1   10/2000

OTHER PUBLICATIONS

The Chemical Society of Japan (CSJ) ed., *Lecture Proceedings II of the 74th Spring Annual Meeting, the Chemical Society of Japan (SCJ),* (Mar. 14, 1998).

* cited by examiner

*Primary Examiner*—Kenneth R. Horlick
*Assistant Examiner*—Joyce Tung
(74) *Attorney, Agent, or Firm*—Peter F. Corless; Christine C. O'Day; Edwards Angell Palmer & Dodge LLP

(57) ABSTRACT

A method for screening the effect of a segment A (chemical species A) on a substance (for example, a cell) containing DNA or RNA by using artificial chemical species. Namely, a method of detecting or identifying the function of a chemical species A on a substance containing DNA or RNA by using one or more chemical species represented by the following general formula (I) which are capable of recognizing a DNA base sequence; a kit therefor; and a plate to be used therein: B-L-A (I) wherein B represents a chemical structure containing an non-natural base capable of recognizing a DNA base sequence; A represents a chemical structure having an interaction with DNA; and L represents a linker whereby the chemical structures A and B can be linked together.

2 Claims, 5 Drawing Sheets

Fig. 2

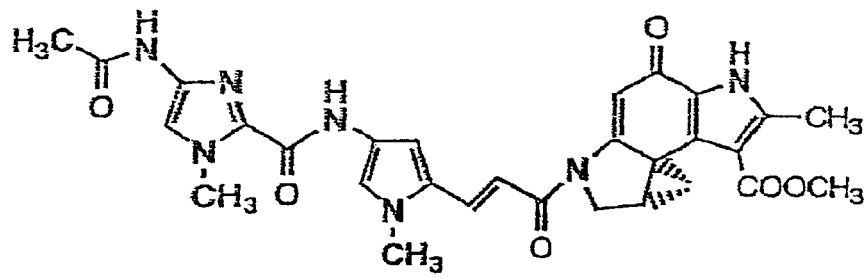

```
5'*_ AGAATCAGGG GATAACGCAG GAAAGAACAT GTGAGCAAAA GGCCAGCAAA
3'_ TCTTAGTCCC CTATTGCGTC CTTTCTTGTA CACTCGTTTT CCGGTCGTTT

AGGCCAGGAA CCGTAAAAAG GCCGCGTTGC TGGCGTTTTT CCATAGGCTC
    TCCGGTCCTT GGCATTTTTC CGGCGCAACG ACCGCAAAAA GGTATCCGAG
                site 1 ↓              site 2 ↓
    CGCCCCCCTG ACGAGCATCA CAAAAATCGA CGCTCAAGTC AGAGGTGGCG
    GCGGGGGGAC TGCTCGTAGT GTTTTTAGCT GCGAGTTCAG TCTCCACCGC
            ↑                    ↑
    AAACCCGACA GGACTATAAA GATACCAGGC GTTTCCCCT GGAAGCTCCC
    TTTGGGCTGT CCTGATATTT CTATGGTCCG CAAAGGGGA CCTTCGAGGG TCGTGCGCTC TCCTGTTCCG ACCCTGCCGC TTACCGGATA CCTGTCCGCC
    AGCACGCGAG AGGACAAGGC TGGGACGGCG AATGGCCTAT GGACAGGCGG TTTCTCCCTT CGGGAAGCGT GGCGCTTTCT CAATGCTCAC GCTGTAGGTA
    AAAGAGGGAA GCCCTTAGCA CCGCGAAAGA GTTACGAGTG CGACATCCAT TCTCAGTTCG GTGTAGGTCG TTCGCTCCAA GCTGGGCTGT GTGCACGAAC
    AGACTCAAGC CACATCCAGC AAGCGAGGTT CGACCCGACA CACGTGCTTG CCCCCGTTCA GCCCGACCGC TGCGCCTTAT CCGGTAACTA TCGTCTTGAG
    GGGGGCAAGT CGGGCTGGCG ACGCGGAATA GGCCATTGAT AGCAGAACTC TCCAACCCGG TAAGACACGA CTTATCGCCA CTGGCAGCAG CCACTGGTAA-3'
    AGGTTGGGCC ATTCTGTGCT GAATAGCGGT GACCGTCGTC GGTGACCATT-5'*
```

Fig. 4
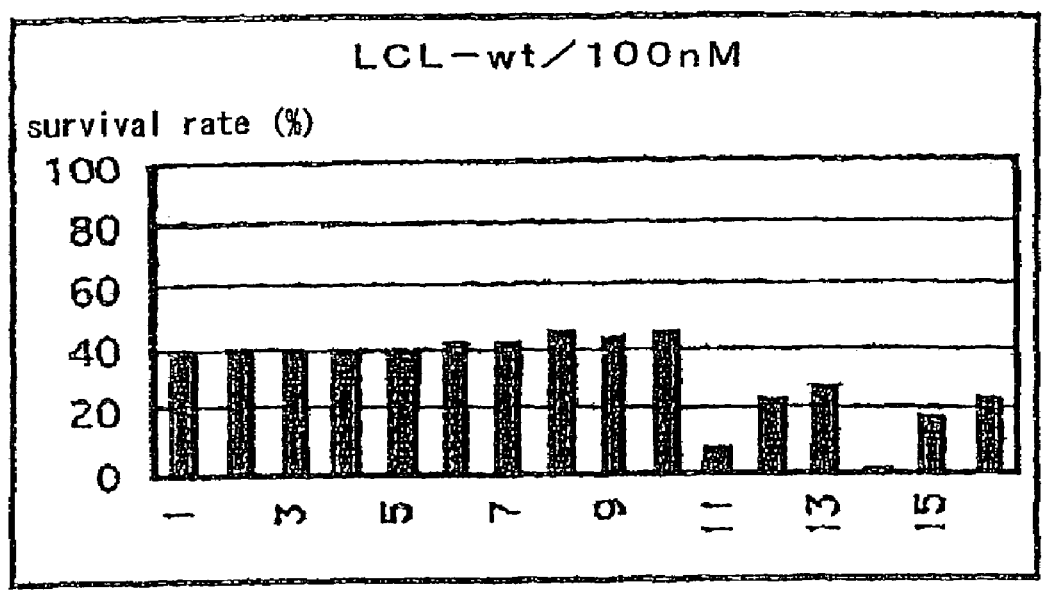
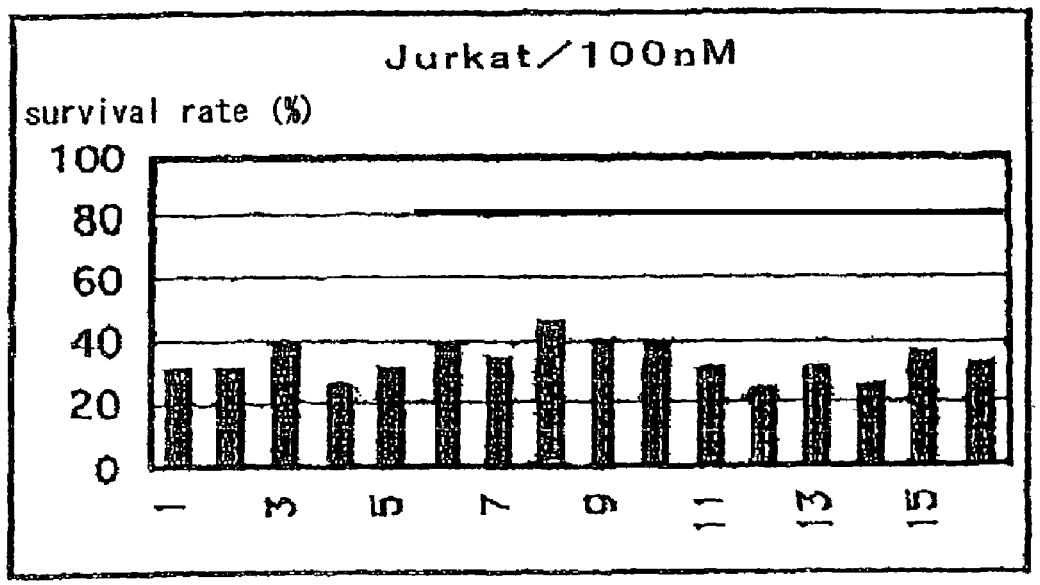

DEVELOPMENT OF METHOD FOR SCREENING PHYSIOLOGICALLY ACTIVE PYRROLE IMIDAZOLE DERIVATIVE

This application is a divisional application of U.S. Ser. No. 09/889,379, filed on Jul. 16, 2001 (U.S. Pat. No. 6,974,668 issued on Dec. 13, 2005) which in turn was a U.S. national stage application of PCT/JP007992, filed Nov. 13, 2000.

TECHNICAL FIELD

The present invention relates to a method for detecting or identifying an action for substances containing DNA or RNA such as cells, using a chemical species having a chemical structure containing non-natural base which can recognize base sequences of natural DNA or RNA, a kit therefor and a plate to be used therefor.

BACKGROUND ART

As a result of studies conducted by the human genome project, base sequences of the full set of genes, "a draft of the human life", will be elucidated within a few years. It is known that diseases or senescence will be developed if the draft has a defect or is injured. As the results of development of the human genome project, many diseases including cancer can be elucidated in a DNA level, and the total medical sciences consisting mainly of diagnosis and prevention are believed to be changed revolutionarily. Further, although we have a great expectation for developments of a therapeutic method based on understanding in DNA levels of diseases and pharmaceuticals targeting in causal genes of the diseases or their products, studies of such fundamental researches mediating to clinical studies have just started. Antitumor drugs used at present are mainly antibiotics selected by screening works, and originally are not the product produced by microorganisms for the purpose of killing tumor cells. Furthermore few drug based on the molecular biological knowledge on tumor has been known. If an expression of an intracellular specific gene can be freely controlled extracellularly, an ultimate therapeutic method in a gene level can be achieved.

We, recently, found that an antibiotic duocarmycin could construct a heterodimer with other kinds of molecules such as distamycin to perform cooperatively molecular recognition of DNA and also perform efficiently an alkylation to a base sequence different from the case of duocarmycin alone (Proc. Natl. Acad. Sci. USA 93, 14405, 1996). Based on the results of this study, we succeeded to synthesize a molecule which could selectively alkylate DNA at any position of its base sequence, by binding pyrrole-imidazole polyamide as a recognition site for DNA to the active alkylation site of duocarmycin, and applied a patent (JP-A-10-260710).

However, the compounds, in which the pyrrole-imidazole polyamide as a DNA recognition site is bound only in the active alkylation site of duocarmycin, are not only insufficient in the alkylation activity but also able only to recognize a single-stranded base sequence. Consequently, we examined alkylation mechanisms between these molecules and DNA in detail using a computer modeling such as molecular dynamics of these compounds, and found that double-stranded DNA could be simultaneously alkylated and cleaved by introducing a linker such as vinyl group into the cyclopropane moiety (segment A), an active site of duocarmycin (JP-A-11-83591).

From the fact that these artificial chemical species, which could recognize base sequences of natural DNA and RNA, recognized a specific base sequence of the natural DNA and RNA, and affected an action of the segment A to the specific site of the DNA and RNA, we found that these artificial chemical species could be applied in place of a partial sequence of the natural DNA and RNA.

DISCLOSURE OF THE INVENTION

An aspect of the present invention is to provide a method for screening an action of the segment A (chemical species A) to substances containing DNA or RNA such as cells by using these artificial chemical species.

The present invention relates to a method for detecting or identifying an action of chemical species A to substance containing DNA or RNA comprising using the chemical species, which can recognize a base sequence of the DNA, represented by the general formula (I):

wherein B is a chemical structure containing non-natural base which can recognize the base sequence of DNA, A is a chemical structure having an interaction with DNA, and L is a linker which can bind together chemical structures of A and B.

More particularly, the present invention relates to a method for detecting or identifying an action of chemical species A to a substance containing DNA or RNA comprising providing the compound represented by the general formula (I), which can recognize a base sequence of DNA or RNA in each well of a plate consisting of a plurality of wells, introducing a substance containing DNA or RNA into each well of said plate, reacting completely with the compound represented by the general formula (I) and the substance containing DNA or RNA, and assaying a state of the substance containing DNA or RNA.

More further particularly, in the method described hereinabove, the present invention relates to a method according to the method described hereinabove wherein the compound represented by the general formula (I) in each well is the compound which can recognize a difference in the base sequence of DNA or RNA of the substance containing DNA or RNA and the substance containing DNA or RNA which is introduced into each well is the same substance.

Further, in the method described hereinabove, the present invention relates to a method according to the method described hereinbefore wherein the compound represented by the general formula (I) in each well is the compound which can recognize a specific type of the base sequence of DNA or RNA of the substance containing DNA or RNA and the substance containing DNA or RNA which is introduced into each well is a different substance.

Further, the present invention relates to a kit for detection or identification of an action of the chemical species A to a substance containing DNA or RNA for carrying out the various methods described hereinbefore.

More particularly, the present invention relates to a kit for detecting or identifying an action of the chemical species A to a substance containing DNA or RNA comprising consisting of the chemical species which can recognize a base sequence of the DNA, represented by the general formula (I):

wherein B is a chemical structure containing non-natural bases which can recognize a base sequence of DNA, A is a chemical structure having an interaction with DNA, and L is a linker which can bind together the chemical structures of A and B;

and equipment or reagents for assaying a state of the substance containing DNA or RNA after treatment.

Further, the present invention relates to a plate consisting of a plurality of wells comprising presence of a chemical species which can recognize a base sequence of DNA, represented by the general formula (I):

B-L-A  (I)

wherein B is a chemical structure containing a non-natural base which can recognize a base sequence of DNA, A is a chemical structure having an interaction with DNA, and L is a linker which can bind together chemical structures of A and B;

in each well in the plate consisting of a plurality of wells, and relates to a plate comprising a plate for detecting or identifying an action of a chemical species A for a substance containing DNA or RNA.

BRIEF DESCRIPTION OF THE DRAWINGS

FIG. 2 shows a base sequence of DNA and a chemical structure of ImPyLDu86 used in the experiment in FIG. 1. (SEQ ID NOS:3-4)

FIG. 4 shows survival rates of tumor cells in the concentrations at 100 nM of the compounds 1-16 of the present invention.

BEST MODE FOR CARRYING OUT THE INVENTION

Figure 1:
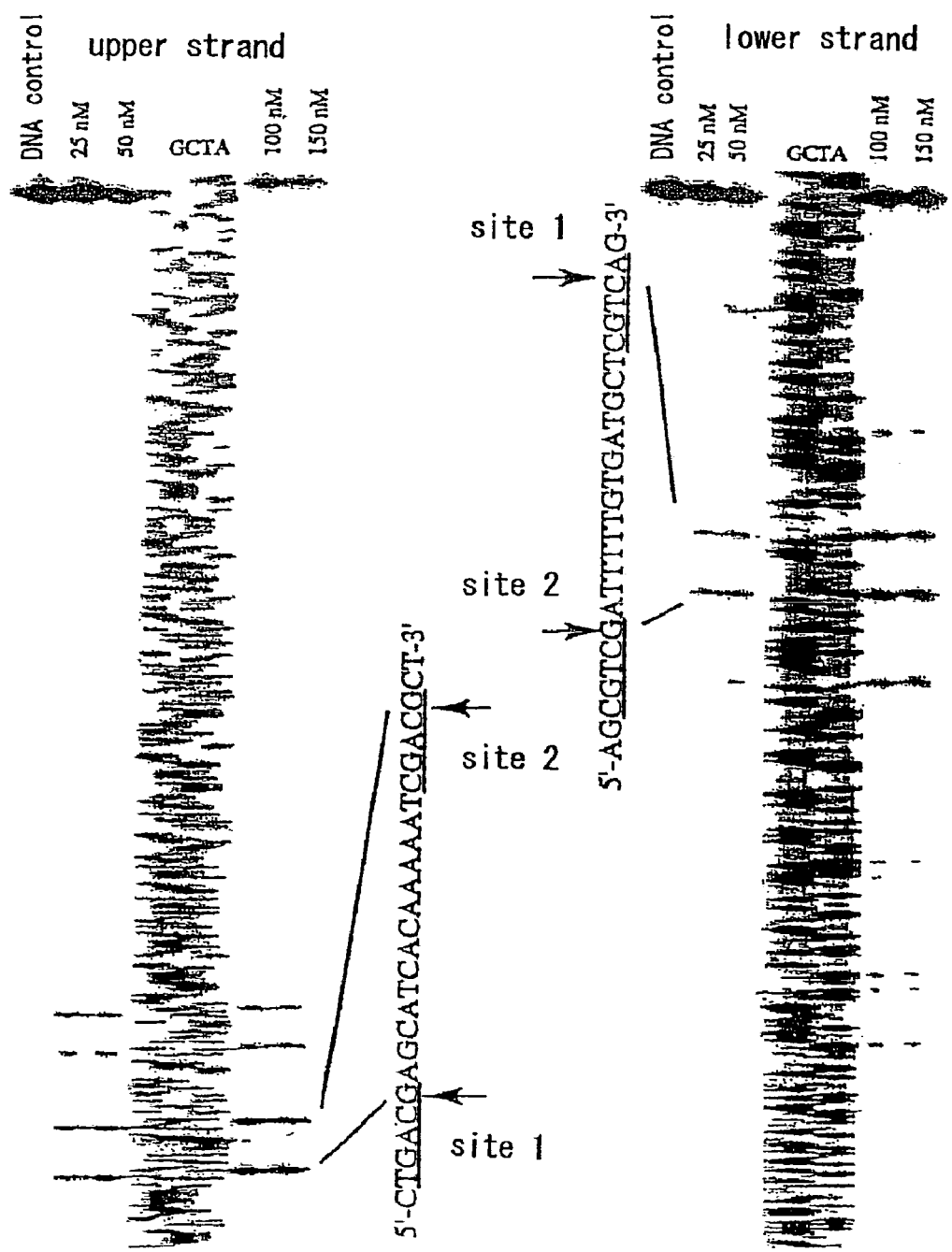
FIG. 1 is a photograph instead of a drawing which shows a result of reaction with ImPyLDu86 of the present invention and DNA (SEQ ID NOS:1-2).

The chemical structure B containing non-natural bases which can recognize a base sequence of DNA in the general formula (I) hereinbefore of the present invention is preferably the chemical structure derived from pyrrole and/or imidazole which may optionally have substituents. Examples of the substituents of pyrrole and imidazole are not limited so long as they do not hinder a recognition of a base sequence of DNA, and are straight or branched alkyl group having 1-10 carbon atoms, preferably 1-5 carbon atoms including, for example, alkoxy group derived from said alkyl group, hydroxyl group, amino group, N-alkyl-substituted amino group derived from said alkyl group, N-acylamino group derived from organic carboxylic acids, guanidino and substituted guanidine groups. More specifically, N-methylpyrrole, N-methylimidazole, 3-hydroxypyrrole, N-methyl-3-hydroxypyrrole, and the like are included.

These non-natural bases which can recognize a natural base sequence may optionally be located in a main chain or may optionally be pendent from a main chain. When these non-natural bases are located in a main chain, these non-natural bases per se may have functional groups for constructing the main chain, for example, a carboxyl group in an end and an amino group in the other end of the non-natural base, and these bases may construct a polyamide structure. The structure constructing the main chain may not be limited within the above polyamide structure, and can be a structure which constructs polyester structure, polyimine structure, and the like.

When these non-natural bases are pendent from a main chain, these bases may be pendent from a structure of polysaccharide such as natural DNA or RNA, or may be pendent from a structure of a synthetic polymer.

Preferable example of the chemical structure B containing non-natural bases, which can recognize a base sequence of DNA, is, more specifically, a pyrrole-imidazole polyamide linkage. Numbers (lengths) of pyrrole and imidazole are not limited, and are preferably about 2-30 units, more preferably about 24-16 units, and further more preferably about 4-16 units.

The chemical structure A, which can bind with a base in DNA, can be a variety of chemical species so long as they can interact with DNA or RNA. Example of the preferable structure of the chemical species (segment A) is a structure of chemical substance having an antitumor activity. Example of a chemical substance having an antitumor activity is preferably alkylating agent for acting to DNA. More preferably, it is a chemical structure having a cyclopropane ring, and further more preferably alkylating moiety of duocarmycin.

The linker moiety L which can bind with the chemical structures A and B may preferably be a structure which can separate the segment A and the segment B with a suitable distance as well as does not inactivate the alkylating activity. Preferable example is a chemical structure having a vinyl group.

The compound represented by the general formula (I) can be used alone or as a mixture of two or more of these compounds. When two or more compounds represented by the general formula (I) are used as a mixture, there may be various mixing patterns. Generally, a mixture of chemical species having different chemical species B (segment B) from each other may be preferable, but is not limited within the same.

Examples of a preferable compound of the present invention represented by the general formula (I) are the compound represented by the following formula (hereinafter designated as "PyPyLDu86"):

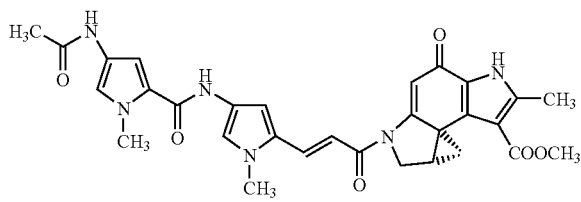

or the compound represented by the following formula (hereinafter designated as "ImPyLDu86"):

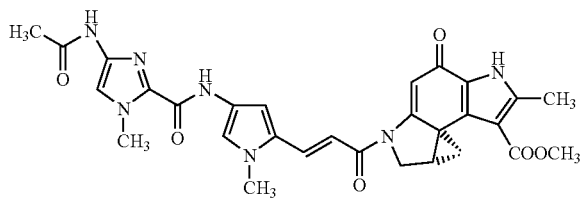

The compounds described hereinabove can recognize sequences such as a base sequence TGACG, or a complementary strand thereof corresponding to ImPyLDu86.

Further, a compound represented by the general formula (II) having a structure of {Py or Im}{Py or Im}LDu86 of the following formula, which is constructed with a basic structure PyPyLDu86:

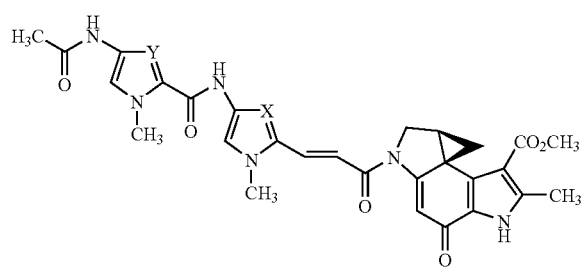

(II)

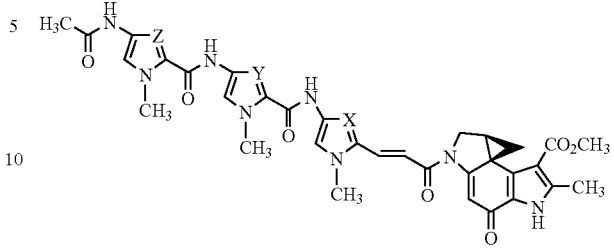

(III)

wherein X and Y are, each independently, —CH= or —N=, or a mixture thereof in the ratio of 1:1 is included.

For the explanations hereinbelow, these compounds or mixtures thereof are numbered as follows.

A compound wherein X is CH and Y is CH is designated as compound 1;

a compound wherein X is CH and Y is N is designated as compound 2;

a compound wherein X is N and Y is CH is designated as compound 3;

a compound wherein X is N and Y is N is designated as compound 4;

a mixture of the compound 1 and the compound 2 in the ratio of 1:1 is designated as compound 5;

a mixture of the compound 1 and the compound 3 in the ratio of 1:1 is designated as compound 6;

a mixture of the compound 1 and the compound 4 in the ratio of 1:1 is designated as compound 7;

a mixture of the compound 2 and the compound 3 in the ratio of 1:1 is designated as compound 8;

a mixture of the compound 2 and the compound 4 in the ratio of 1:1 is designated as compound 9; and a mixture of the compound 3 and the compound 4 in the ratio of 1:1 is designated as compound 10.

Further, a compound represented by the general formula (III) having a structure of {Py or Im}{Py or Im}{Py or Im}LDu86 of the following formula, which is constructed with a basic structure PyPyPyLDu86:

wherein X, Y and Z are, each independently, —CH= or —N=, or a mixture thereof in the ratio of 1:1 can be included.

For the explanations hereinbelow, these compounds or mixtures thereof are numbered as follows.

A compound wherein X is CH, Y is N and Z is N is designated as compound 11;

a compound wherein X is CH, Y is N and Z is CH is designated as compound 12;

a compound wherein X is CH, Y is CH and Z is CH is designated as compound 13;

a mixture of the compound 11 and the compound 12 in the ratio of 1:1 is designated as compound 14;

a mixture of the compound 11 and the compound 13 in the ratio of 1:1 is designated as compound 15; and a mixture of the compound 12 and the compound 13 in the ratio of 1:1 is designated as compound 16.

These compounds 1-16 are used in the experiments described hereinbelow.

The compound represented by the general formula (I) can be produced according to the known methods. Namely, the compound can be produced by producing the segment A and the segment B by the conventional methods; binding the linker segment L successively therewith; and then further binding the remaining segments therewith.

For example, examples of the processes for producing ImPyLDu86 (7a) and PyPyLDu86 (7b) described hereinbefore are illustrated in the following chemical reaction scheme. Numbers below each compound in the reaction scheme show the numbers of those compound.

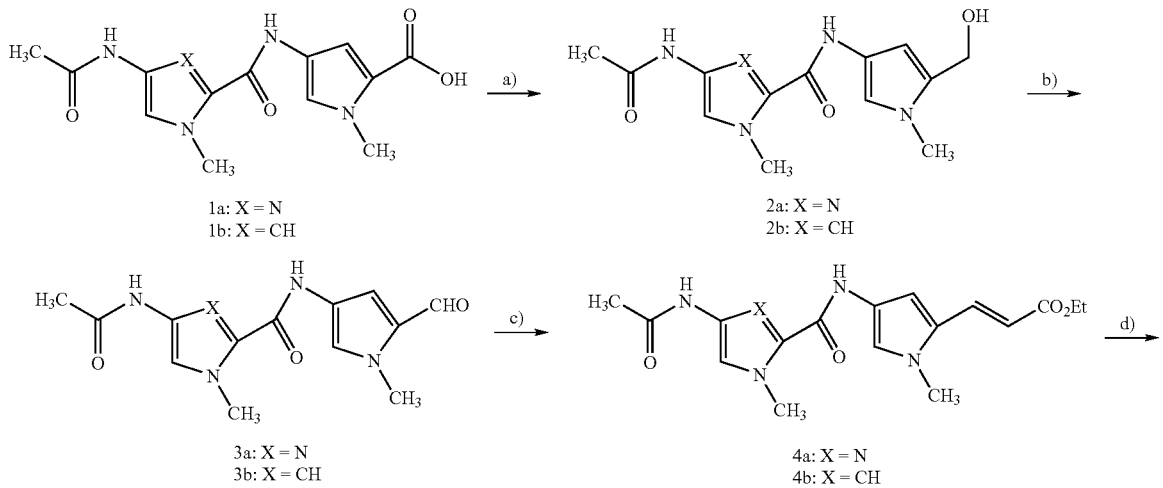

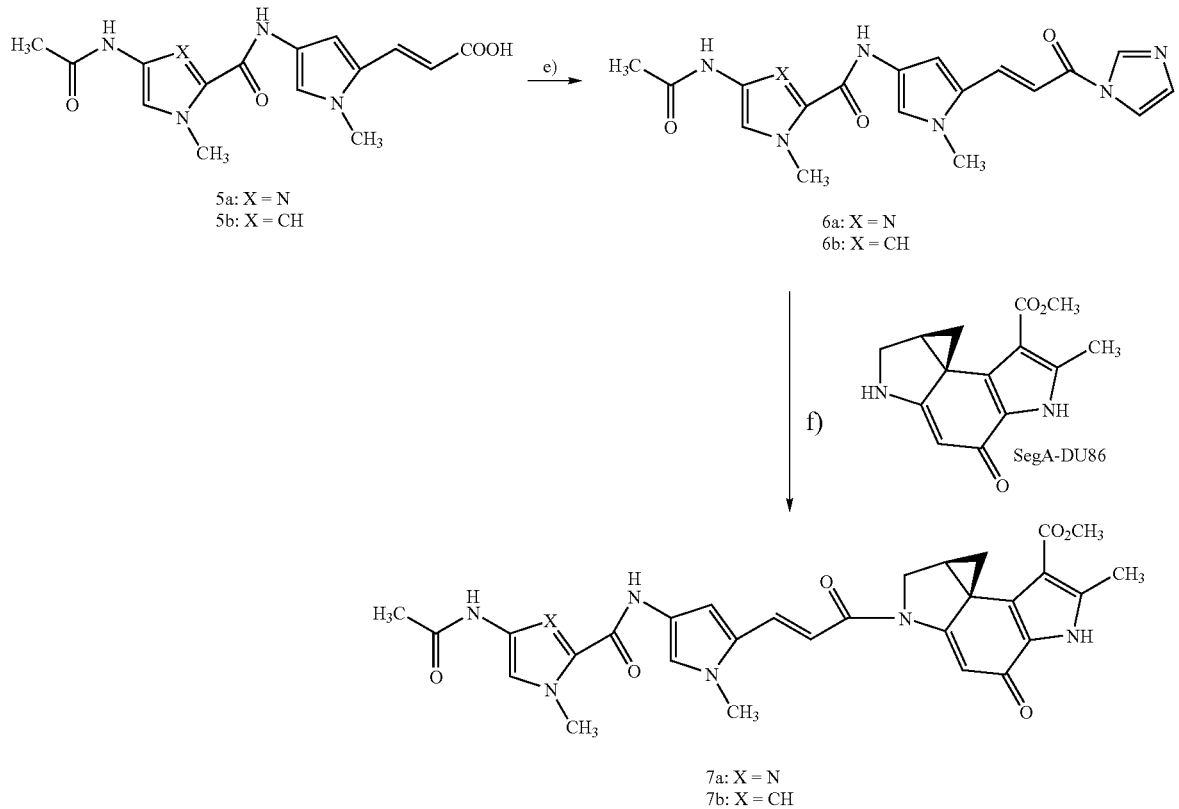

5a: X = N
5b: X = CH

6a: X = N
6b: X = CH

7a: X = N
7b: X = CH

In the reaction scheme; a) indicates treatment with a solution of benzotriazole-1-yl-oxytris (dimethylamino) phosphonium hexafluorophosphate (BOP) in THF, followed by NaBH$_4$ treatment; b) indicates treatment with MnO$_2$ in THF; c) indicates treatment with triethylphosphonoacetate and NaH in THF; d) indicates treatment with sodium hydroxide in aqueous methanol; e) indicates treatment with 1,1-carbonyl-di-imidazole in DMF; and f) indicates treatment of Du86 with the segment A using sodium hydride in DMF.

Reactivities of thus synthesized PyPyLDu86 and ImPy-LDu86 with DNA were determined. Results of alkylation by ImPyLDu86 is shown in FIG. 1. DNA and ImPyLDu86 used in the present experiment are shown in FIG. 2.

In FIG. 1, the left migration pattern shows a result of the upper strand of the double-stranded DNA, and the right migration pattern shows a result of the lower strand of the double-stranded DNA. Locations of alkylation can be observed as cleavage bands by heating. As a result, the double-stranded DNA was cleaved mainly at the site 1 and the site 2 from a low concentration, and it was understood that the alkylation occurred simultaneously in the double-stranded DNA. No compound to generate such a cleavage has been known until now, and it can be surely regarded as an artificial restriction enzyme. Moreover, it was found that the cleavage occurred in such a high ratio as 70%, showing a very high efficiency in comparison with the previously synthesized compounds (JP-A-10-260710).

As for an example of a substance containing DNA or RNA, it is preferable to use living cells although DNA or RNA per se can be used. When an antitumor agent is used as the segment A, tumor cells can be used.

In a case when methylpyrrole (Py) and methylimidazole (Im) are used as non-natural bases in the segment B in the general formula (I), since it is known that a C-G base pair is recognized by Py-Im; a G-C base pair is recognized by Im-Py; and a A-T or a T-A base pair is recognized by Py-Py, an objective base sequence can be recognized by appropriately combining methylpyrrole (Py) and methylimidazole (Tm). Namely, a sequence of natural three bases can be recognized by using three units (trimer) of methylpyrrole (Py) and methylimidazole (Tm), and a sequence of natural four bases can be recognized by using four units (tetramer) of methylpyrrole (Py) and methylimidazole (Tm).

Furthermore, a compound having a sequence of the segment B can be used as a mixture of two or more kinds of them.

In the method of the present invention, an actions of the chemical species A to a substance containing DNA or RNA can be detected or identified by assaying a state of the substance containing DNA or RNA, after reacting completely the compound represented by the general formula (I) with a substance containing DNA or RNA.

As a mean for reacting completely the compound represented by the general formula (I) with a substance containing DNA or RNA, the reaction can be performed by incubating both in a suitable buffer. As a mean for assaying a state of a substance containing DNA or RNA after the incubation, various labeling or coloring methods can be used. These means can be suitably selected depending on a state of a substance containing DNA or RNA.

When living cells are used as a substance containing DNA or RNA, and their state is detected by their survivals, a method for coloring cells is simple and preferable. Quantification of numbers of living cells can be achieved by using commercially available cell counting kit or by combining the kit with a light absorbance in the coloring.

Embodiments of use of the present invention will be explained concretely in the following.

Figure 3:
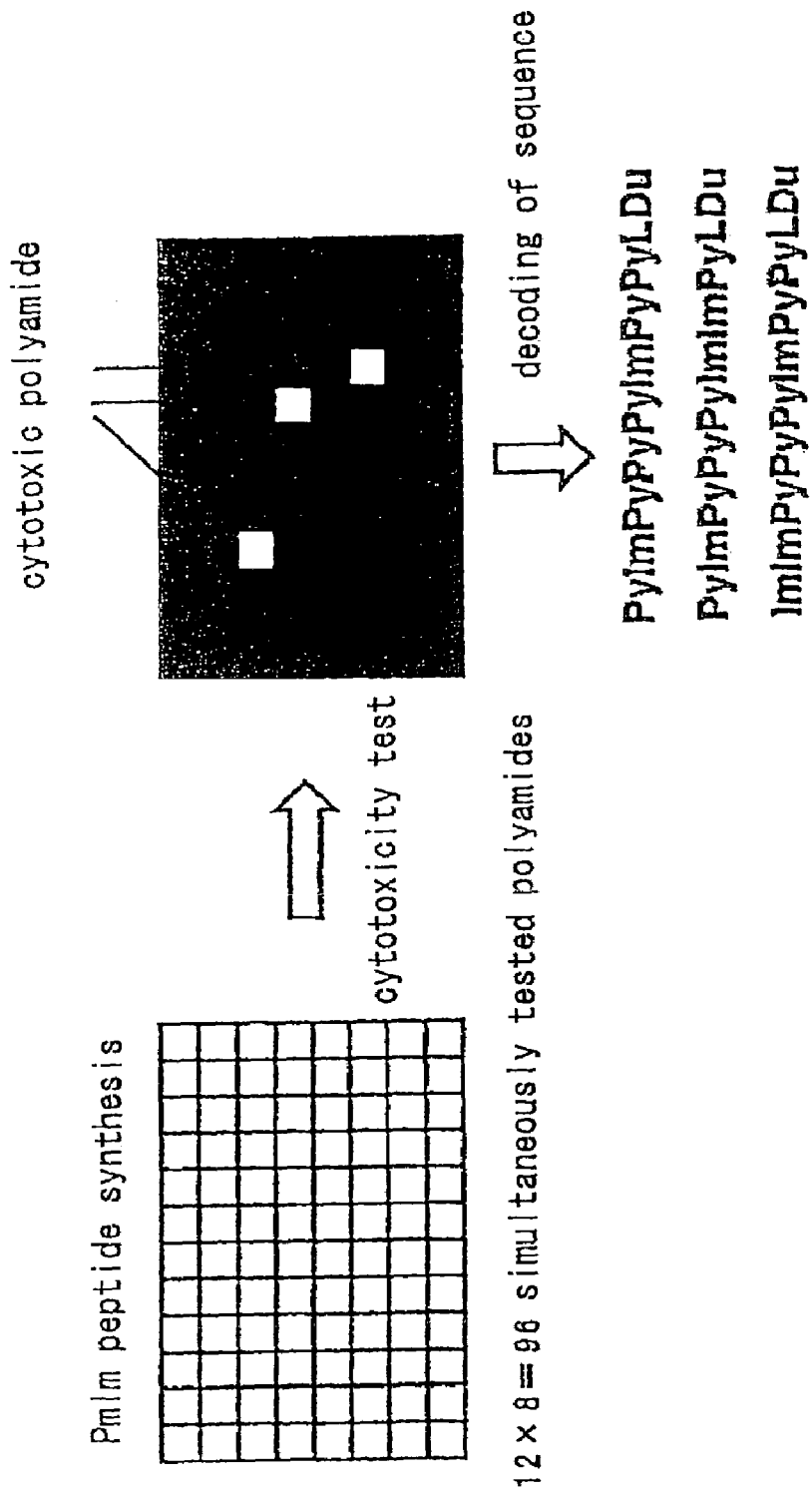
FIG. 3 shows a method for screening antitumor agents specific to tumor cells using the plate of the present invention.

FIG. 3 illustrates a method of the present invention. The left figure in FIG. 3 shown like a section paper is a plate consisting of a plurality of wells, and each square indicates each well In this example, a plate with 96 wells is illustrated. In each well, the chemical species represented by the general formula (I) hereinbefore of the present invention are present. Firstly, a case will be explained wherein the chemical species represented by the general formula (I) of the present invention in each well recognizes different base sequence from each other.

In the case of a tetramer, for example, non-natural bases consisting of methylpyrrole (Py) and methylimidazole (Im) are used in the moiety of the segment B in the chemical species represented by the general formula (I), and a set of bases, which can recognize different three bases, can be prepared by using the structures of all permutations and combinations consisting of Py and Im such as Py-Py-Py-Py, Py-Py-Py-Im, Py-Py-Im-Py and Im-Im-Im-Py (in this case, 16 varieties of combinations can be obtained). An alkylating agent is bound to the segment A of the general formula (I), then the resulting compound is linked with the linker L containing vinyl group.

Then, sixteen types of chemical species having different structures in the segment B are added into each well of the plate shown in the left figure in FIG. 3. Subsequently, tumor cells are added to each well, and incubated for several hours to several days. As a result, the chemical species represented by the general formula (I) recognize a specific region of the base sequences of the tumor cells and reacts with the DNA of tumor cells and alkylating them to kill the tumor cells. In the right figure in FIG. 3, contents of each well are stained after completing the above incubation. Living cells are stained by coloring agents as shown black color in FIG. 3, whereas dead cells can not be stained as shown blank (white) in FIG. 3. The example shown in FIG. 3 is the case in which octamer is used as the segment B, and it is shown that the cancer cells are killed in three types of non-natural base sequences. Since the non-natural base sequence present in each well is known in advance, it can be known by this test in what cases of sequences the tumor cells are killed.

In the case shown in FIG. 3, an octamer is used. Consequently, the chemical species represented by the general formula (I) having $2^8$, i.e. 256 types of the segment B moieties are present in each well. In this case, it is observed that three types of sequences among them can specifically kill the tumor cells. In this case, the three sequences are found to be as follows:

PyImPyPyPyImPyPy,

PyImPyPyPyImImPy, and

ImImPyPyPyImPyPy.

Since tumor cells are different depending on their types and organisms, according to the method described hereinbefore in the present invention, antitumor agents having specific action to the tumor cells as a specimen assayed can be retrieved within a short time in a simple manner. Further, tumor cells, even in the same tissue, may be mutated depending on their stage. Even in such case, an antitumor agent specific to the mutated tumor cells can conveniently be retrieved by the method of the present invention. In addition, according to the method of the present invention described hereinbefore, an action of the antitumor agent to peripheral normal cells of the tumor tissues can also be studied by the same method.

Consequently, the method of the present invention provides a convenient screening method for an antitumor agent having a specific action to the objective tumor cells without affecting normal cells within a short time.

Then, the compounds 1-16 mentioned hereinbefore were assessed for their activities.

Cytotoxicity tests were performed using compounds consisting of 2 or 3 pyrrole (Py) and imidazole (Im) amide moieties in total. Results of effects indicated by survival rates of cells using the compounds 1-16 described hereinbefore are shown in FIG. 4. Simultaneous screening tests using human tumor cells LCL-wt, HLC-2 and human leukemia cell Jurkat showed that only the compound 14 showed high cytotoxicity against LCL-wt and no useful effect was shown against Jurkat and HLC-2.

FIG. 4 shows the test results on cytotoxicities of the compounds 1-16 against LCL-wt and Jurkat at the concentration of 100 nM.

Figure 5:
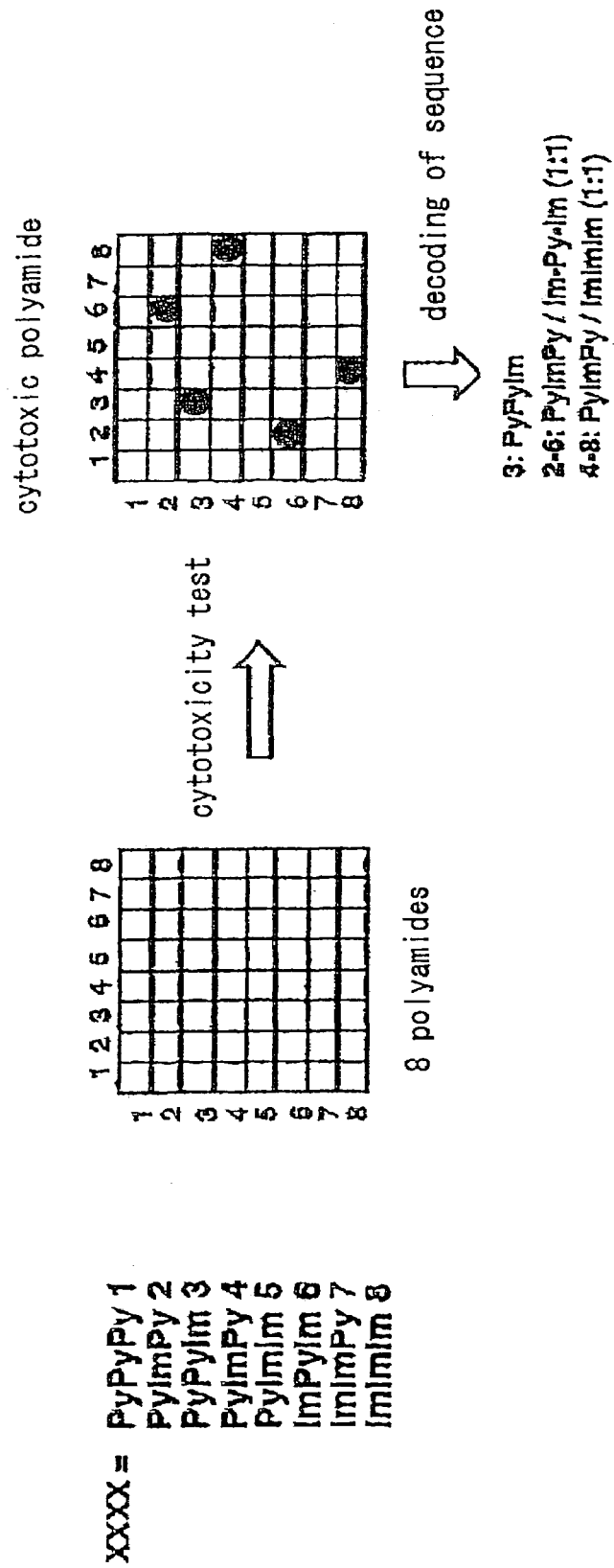
FIG. 5 illustrates a method for testing simultaneously a case using the compounds of the present invention alone and a case using mixture thereof.

As shown above, it became obvious that mixtures of 2 or more compounds represented by the general formula (I) of the present invention showed specific activities. Cases of the test methods using these mixtures are shown in FIG. 5. In FIG. 5, a test using 8×8=64 wells are shown.

Cases with 3 recognition sites in the segment B are illustrated. When pyrrole (Py) and imidazole (Im) are used as the recognition components, combinations of $2^3$ types, i.e. 8 types, can be included. These 8 types, 25 µl each, were added to each well in the lengthwise and the breadthwise. For example, 8 types of compounds were added to each line and row of wells, respectively, in such manner as adding Py-Py-Py, 25 µl each, on the first line and the first row of the plate, then adding Py-Im-Py, 25 µl each, on the second line and the second row of the plate, further adding Py-Py-Im, 25 µl each, on the third line and the third row of the plate. As a result, only one type of the compound was added in the wells on the diagonal line of the plate, and the mixtures consisting of 2 types of compounds in a ratio of 1:1 were added in the wells other than those on the diagonal line. Results of incubation with tumor cells performed by the same method as the method shown in FIG. 3 and treatment with coloring agents are illustrated in FIG. 5.

In the case shown in FIG. 5, death of the tumor cells are observed in the well on the third line and the third row, wells on the second line and the sixth row and on the sixth line and the second row, and wells on the fourth line and the eighth row and on the eighth line and the fourth row. Since the well on the third line and the third row is on the diagonal line, Py-Py-Im alone can be found to kill the tumor cells. Since the wells on the second line and the sixth row and on the sixth line and the-second row and the wells on the fourth line and the eighth row and on the eighth line and the fourth row are located in the symmetrical positions about the diagonal line, the former is a 1:1 mixture of Py-Im-Py and Im-Py-Im and the latter is a 1:1 mixture of Py-Im-Py and Im-Im-Im. In this case, it is shown that the compound or the mixtures having these segments B are specifically effective against these tumor cells.

Further, this experimental case demonstrates an important point that although an efficacy of the compound of the general formula (I) against tumor cells is not shown when the compound is used alone, there is a case showing an efficacy only when used in a mixture with other compound.

According to the test method of the present invention, results of the case using the compound represented by the general formula (I) alone can be obtained, and simultaneously results of the case using these compounds as a mixture can also be obtained.

The above case is the method for retrieving an antitumor agent specific to tumor cells. Further, a chemical species having the segment B moiety represented by the general formula (I) of the present invention corresponding to said base sequence is prepared using tumor cells, of which an efficacy is known at a specific location in the base sequence, as the substance containing DNA or RNA, a plurality of types of chemical species represented by the general formula (I) of the present invention, which are bound with various candidate compounds of an antitumor agent and different each other in their segment A moieties, are provided in each well, then these chemical species are incubated with tumor cells described hereinbefore, thus actions of the candidate compounds in the segment A moieties can be retrieved.

An aspect of the present invention is to provide a screening method for an antitumor action to tumor cells by binding the candidate compound of an antitumor agent to the segment A moiety of the general formula (I) of the present invention.

Further, the present invention provides a kit for detecting or identifying an action of the chemical species A for the substance containing DNA or RNA for performing the various methods of the present invention described hereinbefore.

More particularly, the present invention provides a kit for detecting or identifying an action of the chemical species A to the substance containing DNA or RNA comprising consisting of the chemical species, which can recognize a base sequence of DNA, represented by the general formula (I):

B-L-A           (I)

wherein B is a chemical structure containing non-natural bases which can recognize a base sequence of DNA, A is a chemical structure having an interaction with DNA, and L is a linker which can bind together chemical structures of A and B;

and equipment or reagents for assaying a state of the substance containing DNA or RNA after treatment. As described hereinbefore, the compound of the general formula (I) of the present invention may be used alone or may be prepared to be used as a mixture of 2 or more types of the compounds.

Further, the present invention provides a plate consisting of a plurality of wells comprising providing the chemical species, which can recognize a base sequence of DNA, represented by the general formula (I):

B-L-A           (I)

wherein B is a chemical structure containing non-natural bases which can recognize a base sequence of DNA, A is a chemical structure having an interaction with DNA, and L is a linker which can bind together chemical structures of A and B;

in each well in the plate consisting of a plurality of wells. More particularly, the plate of the present invention is a plate for detecting or identifying an action of the chemical species A to the substance containing DNA or RNA.

The compound represented by the general formula (I) hereinbefore may be of one type or two or more types, being immobilized in each well of the plate. These compounds may also be in a state of solution or gel.

The present invention will be explained in detail by concrete examples, but is not limited within these concrete examples.

EXAMPLES

Example 1

Assessment of Antitumor Effect by Cytotoxicity Test

Human tumor cells LCL-wt and HLC-2, human leukemia cell, Jurkat, and human cervix cancer cell HeLa cell were used as tumor cells. For LCL-wt and Jurkat, PRMI 1640 (Gibco BRL)+10% fetal bovine serum (JRH BIOSCIENCES)+100 µU/ml penicillin G–100 µU/ml streptomycin sulfate (Gibco BRL) were used as the medium for incubation. For HLC-2, MEM+10% fetal bovine serum (JRH BIOSCIENCES)+100 µU/ml penicillin G–100 µU/ml streptomycin sulfate (Gibco BRL) were used as the medium for incubation. For HeLa cell, RBMI+10% fetal bovine serum (JRH BIOSCIENCES)+100 µU/ml penicillin G–100 µU/ml streptomycin sulfate (Gibco BRL) were used as the medium for incubation. Respective cells were incubated and cells with the logarithmic growth phase were suspended and used for screening.

The screening was carried out as follows. Cell suspension adjusted to the initial cell counts at approximately $2 \times 10^5$ cells/ml was added separately into 96 wells of multi-plate at 50 µl/well. The test solution of the test compound (100 µM, medium+0.1% DMSO) was added thereto and incubated at 37° C., under 5% $CO_2$ concentration, for 2 days in the incubator, then cell counts were counted.

Cell counts were calculated using a micro plate reader (MPR-A4i, TOSOH) and a hemocytometer. In an assay using the micro plate reader, the cell counting kit-8 (DOJINDO) was used, and light absorbance was measured at 450 nm (reference wave length 600 nm). Viable cell counts and inviable cell counts were performed by the dye exclusion test using trypan blue under a microscope. Based on the results of measuring using the micro plate reader and the hemocytometer, survival rate was calculated by the following formula:

Survival rate=100 $n_p/n_a$ wherein $n_p$ is the viable counts with addition of sample and $n_a$ is the control viable counts.

Example 2

Cytotoxicity Test

Simultaneous screening tests were performed using human tumor cells LCL-wt, HLC-2 and human leukemia cell Jurkat with the plate of the present invention using the compounds 1-16 described hereinbefore.

Results were treated in the same way as in Example 1 and survival rate of each cell was calculated.

In FIG. 4, results of the test compounds at the concentration of 100 nM are shown.

The results indicate that the compound 14 shows a high cytotoxic action only against LCL-wt.

Example 3

Synthesis of Compounds

The method of synthesis of the compound 13 is illustrated as follows.

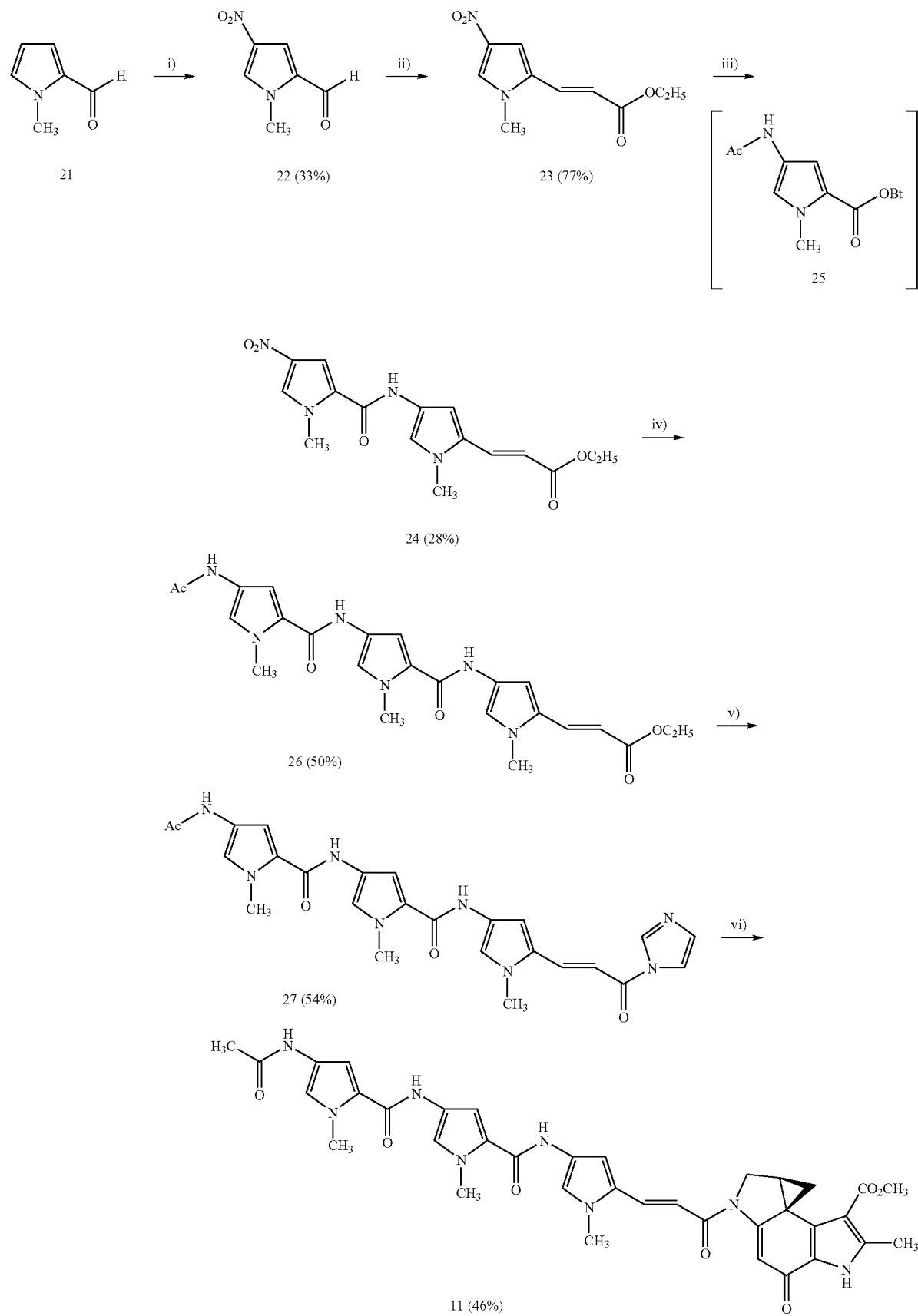

The commercially available materials were used for reagents used in the reactions and the purifications and solvents. For proton nuclear magnetic resonance spectra (NMR), Nihon Denshi JNM-A500 was used. Tetramethylsilane (TMS) was used as an internal standard substance and chemical shifts were shown by δ-value (ppm). Abbreviations for signals are shown as follows: s (singlet), d (doublet), t (triplet), q (quartet), m (multiplet), br (broad) and br s (broad singlet). Abbreviations of reagents and solvents are as follows: dimethylformamide (DMF), dicyclohexylcarbodiimide (DCC), carbonyldiimidazole (CDI), 4-(dimethyl) aminopyridine (DMAP), N-hydroxybenzotriazole (HOBt), 1-[3-(dimethylamino) propyl]-3-ethylcarbodiimidide hydrochloride (EDCI) and tetrahydrofuran (THF). The reactions were performed, if not specified, under an argon atmosphere or a nitrogen atmosphere.

(1) 1-methyl-4-nitro-pyrrole-2-aldehyde (22)

Acetic anhydride (25 ml) solution of fuming nitric acid (1.5 ml, 37.5 mmol) was cooled at −30° C. Acetic anhydride (10 ml) solution of 1-methylpyrrole-2-carboxyaldehyde (21) (3.27 g, 30.0 mmol) was dropwisely added under the same temperature, and the mixture was stirred at the same temperature for 5 hours. The precipitated solid was filtered to obtain nitro compound (22) (860 mg, 19%). The solvent of the filtrate was removed in vacuo, and the obtained residue was charged on a silica gel column chromatography to obtain an additional (22) (650 mg, 14%) from hexane-ethyl acetate (4:1, v/v) eluate.

$^1$H NMR (CDCl$_3$) δ: 4.00(3H,s), 7.40(1H,d,J=2.0 Hz), 7.65(1H,d,D=2.0 Hz), 9.6 1((1H,s);

IR (KBr) ν: 1678, 1535, 1508, 1423, 1406, 1311, 1100, 864, 814, 770, 754cm$^{-1}$ (2) Py-L-CO$_2$Et (23)

Sodium hydride (83 mg, 2.1 mmol) was added to THF (15 ml) solution of triethyl phosphonoacetate (0.39 ml, 2.0 mmol) under ice cooling and stirred for 10 minutes. THF (5 ml) solution of nitro compound (22) was dropwisely added at the same temperature, and stirred at the same temperature for further 45 minutes. Water was added to the reaction mixture and extracted with ethyl acetate. The organic layer was washed with saturated aqueous sodium chloride solution and dried by adding anhydrous magnesium sulfate. The solvent was distilled off in vacuo, and the obtained residue was charged on a silica gel column chromatography to obtain ester (23) (225 mg, 77%) from hexane-ethyl acetate (1:4, v/v) eluate.

$^1$H NMR (CDCl$_3$) δ: 1.28(3H,t,J=7.5 Hz), 3.75(3H,s), 4.24(2H,q,J=7.5 Hz), 6.28(1H,d,J=16.0 Hz), 7.09(1H,d, J=2.0 Hz), 7.47(1H,d,J=16.0 Hz), 7.54(1H,d,J=2.0 Hz);

$^{13}$C NMR (CDCl$_3$) δ: 14.3, 35.4, 60.8, 106.1, 118.4, 125.3, 129.8, 130.1, 136.7, 166.5;

IR (KBr) ν: 1709, 1632, 1510, 1427, 1412, 1373, 1315, 1282, 1176 cm$^{-1}$ (3) Py-Py-L-CO$_2$Et (24)

To methanol solution (45 ml) of the ester (23) (1.12 g, 5.0 mmol), 10% palladium carbon (250 mg) was added at room temperature. 1 N-sodium borohydride (8 ml) was added to the mixture at the same temperature and stirred for further 10 minutes. After addition of acetone (2 ml), the suspension was passed through Celite and the precipitate was removed. The solvent of the filtrate was distilled off in vacuo and ethyl acetate was added to the obtained residue. The solution was washed with aqueous saturated sodium chloride solution and dried by adding anhydrous magnesium sulfate. The solvent was distilled off in vacuo. The obtained residue was dissolved in methylene chloride (45 ml) and was used for the subsequent reaction. 1-methyl-4-nitro-2-trichloroacetylpyrrole (2.35 g, 7.0 mmol) and N,N-diisopropylethylamine (1.31 ml, 7.5 mmol) were gradually added to the solution at room temperature and stirred at the same temperature for 3 hours. Water was added to the reaction mixture and extracted with ethyl acetate. The organic layer was washed with aqueous saturated sodium chloride solution and dried by adding anhydrous magnesium sulfate. The solvent was distilled off in vacuo. The obtained residue was charged on a silica gel column chromatography to obtain bispyrrole (24) (483 mg, 28%) from the ethyl acetate eluate.

$^1$H NMR (CDCl$_3$+DMSO-d$_6$) δ: 1.23(3H,t,J=7.0 Hz), 3.59(3H,s), 3.94(3H,s), 4.14(2H,q,J=7.0 Hz), 6.01(1H,d, J=15.5 Hz), 6.57(1H,d,J=2.0 Hz), 7.27(1H,br s), 7.45(1H, d,J=15.5 Hz), 7.46(1H,d,J=1.5Hz), 7.50(1H,d,J=2.0 Hz), 9.59(1H,br s)

(4) Py-Py-Py-L-CO$_2$Et (26)

To the suspension of bispyrrole (24) (173 mg, 0.50 mmol) in methanol-ethyl acetate (10 ml-10 ml), 10% palladium carbon (50 mg) was added at room temperature. 1 N sodium borohydride (1.5 ml) was added to the mixture at the same temperature and stirred for further 2 minutes. The suspension was passed through a silica gel column chromatography to remove the precipitate. The solvent was distilled off in vacuo. The obtained residue was dissolved in DMF (10 ml) and was used for the subsequent reaction. 4-acetamino-1-methylpyrrole-2-carboxylate HOBt ester (25) [Z. -F. Tao, et al., J. Am. Chem. Soc., 121, 4961-4967 (1999)] (209 mg, 0.70 mmol) and DMAP (85 mg, 0.70 mmol) were gradually added to the solution and the mixture was stirred at the same temperature for 3 hours. The solvent was distilled off in vacuo and the obtained residue was subjected to a silica gel column chromatography. Tris-pyrrole (26) (120 mg, 50%) was obtained from methanol-ethyl acetate (1:9, v/v) eluate.

$^1$H NMR (CDCl$_3$) δ: 1.29(3H,t,J=7.0 Hz), 2.06(3H,s), 3.59 (3H,s), 3.81(3H,s), 3.84(3H,s), 4.20(2H,q,J=7.0 Hz), 5.99 (1H,d,J=15.5 Hz), 6.51(1H,s), 6.58(1H,s), 6.61(1H,s), 6.94(1H,d,J=2.0 Hz), 7.13(1H,s), 7.32(1H,d,J=2.0 Hz), 7.47(1H,d,J=15.5 Hz), 7.78(1H,s), 7.98(1H,s), 8.36(1H,s)

(5) Py-Py-Py-L-CO$_2$Im (27)

Aqueous 1 N sodium hydroxide solution (1.5 ml) was added to methanol-THF (10 ml-10 ml) solution of tris-pyrrole (26) (24 mg, 0.050 mmol) at room temperature, and stirred at room temperature for 5 hours. The solvent was distilled off in vacuo. Aqueous 10% acetic acid solution was added to the obtained residue and the precipitate was filtered to obtain the hydrolysate (13.5 mg). The hydrolysate was used in the next reaction step without further purification. CDI (24.3 mg, 0.15 mmol) was added to DMF (1.5 ml) solution of the hydrolysate (12.8 mg) at room temperature and stirred at the same temperature overnight. Water was added and the precipitate was filtered to obtain imidazole ester (27) (13.5 mg, 54%).

$^1$H NMR (DMSO-d$_6$)δ: 1.96(3H,s), 3.77(3H,s), 3.82((3H,s), 3.85(3H,s), 6.85(1H,s), 7.08(1H,s), 7.09(1H,s), 7.12(1H,d,J=15.0 Hz), 7.14(1H,s), 7.22(1H,s), 7.24(1H,s), 7.47(1H,s), 7.87(1H,d,J=15.0 Hz), 7.90(1H,s), 8.66(1H,s), 9.80(1H,s), 9.89(1H,s), 10.03(1H,s)

(6) Py-Py-Py-L-Du86 (11)

60% sodium hydride (2.0 mg, 0.050 mmol) was added to DMF (2 ml) solution of Du86 A segment (28)[S. Nakamura, et al., J. Med. Chem., 40, 972-979 (1999)] (6.2 mg, 0.024 mmol) under ice cooling and stirred at the same temperature for 10 minutes. Then DMF (1 ml) solution of imidazole ester (27) (12.9 mg, 0.026 mmol) was added at the same temperature and stirred at the same temperature for further 5 hours. After adding sodium phosphate buffer (pH 6.86), water was added and extracted with methylene chloride. The solvent was distilled off in vacuo and the obtained residue was subjected to a silica gel column chromatography. Py-Py-Py-L-Du86 (11) (7.7 mg, 46%) was obtained from methanol-chloroform (1:9, v/v) eluate.

$^1$H NMR (DMSO-$d_6$)δ: 1.29-1.31(1H,m), 1.97(3H,s), 2.07-2.11(1H,m), 2.47(3H,s), 3.72(3H,s), 3.78(3H,s), 3.82(3H,s), 3.83(3H,s), 4.17-4.22(1H,m), 4.27-4.32(1H,m), 6.57(1H,d,J=15.0 Hz), 6.83-6.85(br s), 6.86(1H,s), 6.90(1H,s), 7.06(1H,s), 7.15(1H,s), 7.24(1H,s), 7.39(1H,s), 7.57(1H,d, J=15.0 Hz), 9.80(1H,s), 9.89(1H,s), 9.94(1H,s), 12.36(1H,s)

INDUSTRIAL APPLICABILITY

The present invention provides a method for screening a substance specifically acting to specific cells by a simple method within a short time with a high sensitivity as well as by means of an inexpensive mean, a kit and a plate therefor. According to the method of the present invention, drugs acting specifically to cells of patients, for example tumor cells, can be known within a short time. Consequently, tailor-made drugs for treatment depending on tumor cells of an individual patient can be created, and curative drugs with less side effect and a high efficacy for the patient can be provided Further, according to the method of the present invention, substances acting to DNA or RNA can be screened conveniently highly sensitively and inexpensively. In addition, a site of action in DNA and RNA of the substance, in which an action to DNA or RNA has been known, can easily be known by the method of the present invention.

The invention claimed is:

1. A plate consisting of a plurality of wells, each well comprising a chemical species, which can recognize a base sequence of DNA, wherein the chemical species is represented by the general formula (IV):

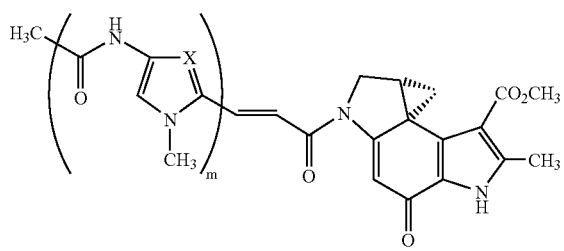

(IV)

wherein m is 2 to 30, and each occurrence of X is independently selected from —CH= or —N=.

2. The plate according to claim 1, wherein a substance containing DNA or RNA is introduced into each well of the plate comprising the chemical species such that an action of the chemical species to the substance containing DNA or RNA may be detected or identified.

* * * * *

```
                       SEQUENCE LISTING

<160> NUMBER OF SEQ ID NOS: 4

<210> SEQ ID NO 1
<211> LENGTH: 27
<212> TYPE: DNA
<213> ORGANISM: Human

<400> SEQUENCE: 1
ctgacgagca tcacaaaaat cgacgct                                          27

<210> SEQ ID NO 2
<211> LENGTH: 27
<212> TYPE: DNA
<213> ORGANISM: Human

<400> SEQUENCE: 2
agcgtcgatt tttgtgatgc tcgtcag                                          27

<210> SEQ ID NO 3
<211> LENGTH: 450
<212> TYPE: DNA
<213> ORGANISM: Human

<400> SEQUENCE: 3
agaatcaggg gataacgcag gaaagaacat gtgagcaaaa ggccagcaaa aggccaggaa      60
ccgtaaaaag gccgcgttgc tggcgttttt ccataggctc cgcccccctg acgagcatca     120
caaaaatcga cgctcaagtc agaggtggcg aaacccgaca ggactataaa gataccaggc     180
gtttccccct ggaagctccc tcgtgcgctc tcctgttccg accctgccgc ttaccggata     240
cctgtccgcc tttctccctt cgggaagcgt ggcgctttct caatgctcac gctgtaggta     300
tctcagttcg gtgtaggtcg ttcgctccaa gctgggctgt gtgcacgaac cccccgttca     360
gcccgaccgc tgcgccttat ccggtaacta tcgtcttgag tccaacccgg taagacacga     420
cttatcgcca ctggcagcag ccactggtaa                                     450

<210> SEQ ID NO 4
<211> LENGTH: 450
<212> TYPE: DNA
<213> ORGANISM: Human

<400> SEQUENCE: 4
ttaccagtgg ctgctgccag tggcgataag tcgtgtctta ccgggttgga ctcaagacga      60
```

```
tagttaccgg ataaggcgca gcggtcgggc tgaacgggg gttcgtgcac acagcccagc    120
ttggagcgaa cgacctacac cgaactcaga tacctacagc gtgagcattg agaaagcgcc   180
acgattcccg aagggagaaa ggcggacagg tatccggtaa gcggcagggt cggaacagga   240
gagcgcacga gggagcttcc aggggggaaac gcctggtatc tttatagtcc tgtcgggttt   300
cgccacctct gacttgagcg tcgattttg tgatgctcgt caggggggcg gagcctatgg    360
aaaaacgcca gcaacgcggc cttttacgg ttcctggcct tttgctggcc ttttgctcac    420
atgttctttc ctgcgttatc ccctgattct                                     450
```